(12) United States Patent
Kinsho et al.

(10) Patent No.: US 6,746,818 B2
(45) Date of Patent: Jun. 8, 2004

(54) (METH)ACRYLATES HAVING LACTONE STRUCTURE, POLYMERS, PHOTORESIST COMPOSITIONS AND PATTERNING PROCESS

(75) Inventors: Takeshi Kinsho, Niigata-ken (JP); Koji Hasegawa, Niigata-ken (JP); Takeru Watanabe, Niigata-ken (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 10/167,444

(22) Filed: Jun. 13, 2002

(65) Prior Publication Data
US 2003/0008232 A1 Jan. 9, 2003

(30) Foreign Application Priority Data
Jun. 14, 2001 (JP) ........................................ 2001-179614

(51) Int. Cl.$^7$ ............................................... G03F 7/004
(52) U.S. Cl. .................... 430/270.1; 430/325; 430/905; 526/281; 526/316; 549/263; 549/265
(58) Field of Search ............................. 430/270.1, 325, 430/905; 526/281, 319; 549/263, 265

(56) References Cited

U.S. PATENT DOCUMENTS 6,280,898 B1 * 8/2001 Hasegawa et al. ........ 430/270.1
6,461,788 B1 * 10/2002 Miwa et al. ............. 430/270.1
2001/0026901 A1 * 10/2001 Maeda et al.

\* cited by examiner

*Primary Examiner*—Rosemary Ashton
(74) *Attorney, Agent, or Firm*—Millen, White, Zelano & Branigan, P.C.

(57) ABSTRACT

(Meth)acrylate compounds having a norbornane, bicyclo[2.2.2]octane, 7-oxanorbornane or cyclohexane ring structure and a γ-butyrolactone ring structure connected together by a suitable linker are novel and useful in forming polymers having high transparency, especially at the exposure wavelength of an excimer laser.

20 Claims, No Drawings

(METH)ACRYLATES HAVING LACTONE STRUCTURE, POLYMERS, PHOTORESIST COMPOSITIONS AND PATTERNING PROCESS

This invention relates to (i) a novel (meth)acrylate compound having a lactone structure useful as a monomer for polymerization, (ii) a polymer obtained therefrom, (iii) a photoresist composition, especially a chemically amplified photoresist composition, comprising the polymer as a base resin and suited for photolithographic microfabrication, and (iv) a patterning process using the photoresist composition.

BACKGROUND OF THE INVENTION

While a number of recent efforts are being made to achieve a finer pattern rule in the drive for higher integration and operating speeds in LSI devices, deep-ultraviolet lithography is thought to hold particular promise as the next generation in microfabrication technology. In particular, photolithography using a KrF or ArF excimer laser as the light source is strongly desired to reach the practical level as the micropatterning technique capable of achieving a feature size of 0.3 μm or less.

The resist materials for use in photolithography using light of an excimer laser, especially ArF excimer laser having a wavelength of 193 nm, are, of course, required to have a high transparency to light of that wavelength. In addition, they are required to have an etching resistance sufficient to allow for film thickness reduction, a high sensitivity sufficient to eliminate any extra burden on the expensive optical material, and especially, a high resolution sufficient to form a precise micropattern. To meet these requirements, it is crucial to develop a base resin having a high transparency, rigidity and reactivity. None of the currently available polymers satisfy all of these requirements. Practically acceptable resist materials are not yet available.

Known high transparency resins include copolymers of acrylic or methacrylic acid derivatives and polymers containing in the backbone an alicyclic compound derived from a norbornene derivative. All these resins are unsatisfactory. For example, copolymers of acrylic or methacrylic acid derivatives are relatively easy to increase reactivity in that highly reactive monomers can be introduced and acid labile units can be increased as desired, but difficult to increase rigidity because of their backbone structure. On the other hand, the polymers containing an alicyclic compound in the backbone have rigidity within the acceptable range, but are less reactive with acid than poly(meth)acrylate because of their backbone structure, and difficult to increase reactivity because of the low flexibility of polymerization. Additionally, since the backbone is highly hydrophobic, these polymers are less adherent when applied to substrates. Therefore, some resist compositions which are formulated using these polymers as the base resin fail to withstand etching although they have satisfactory sensitivity and resolution. Some other resist compositions are highly resistant to etching, but have low sensitivity and low resolution below the practically acceptable level.

SUMMARY OF THE INVENTION

An object of the invention is to provide a novel (meth)acrylate compound having a lactone structure useful as a monomer to form a polymer for use in the formulation of a photoresist composition which exhibits firm adhesion and high transparency when processed by photolithography using light with a wavelength of less than 300 nm, especially ArF excimer laser light as the light source. Another object of the invention is to provide a polymer obtained from the (meth)acrylate compound, a photoresist composition comprising the polymer, and a resist patterning process.

We have found that a (meth)acrylate compound having a lactone structure of formula (1), (2), (3), (4) or (5) can be prepared in high yields by a simple method to be described later, that a polymer obtained from this (meth)acrylate compound has high transparency at the exposure wavelength of an excimer laser, and that a resist composition comprising the polymer as a base resin is improved in adhesion to substrates.

In a first aspect, the present invention provides a (meth)acrylate compound having the following general formula (1).

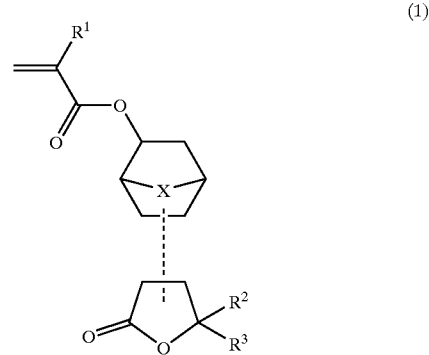

(1)

Herein, $R^1$ is hydrogen or methyl, $R^2$ and $R^3$ each are hydrogen or a straight, branched or cyclic alkyl group having 1 to 15 carbon atoms, or $R^2$ and $R^3$, taken together, may form a ring and in that event, $R^2$ and $R^3$ together represent a straight, branched or cyclic alkylene group having 2 to 15 carbon atoms, X is —$CH_2$—, —$CH_2CH_2$— or —O— or two separate —H, and the broken line represents a single bond or divalent organic group that connects the norbornane ring, bicyclo[2.2.2]octane ring, 7-oxanorbornane ring or cyclohexane ring structure to the γ-butyrolactone ring structure, or a structure that shares one or two constituent carbon atoms between these ring structures.

Preferred (meth)acrylate compounds have the following general formula (2).

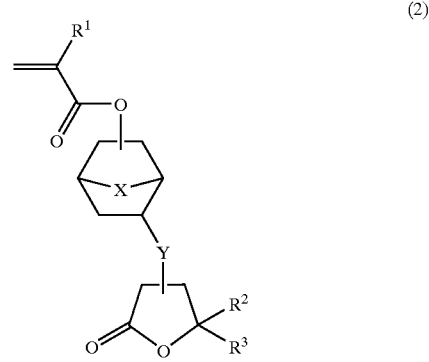

(2)

Herein, $R^1$, $R^2$, $R^3$, and X are as defined above, and Y is —$(CH_2)_n$— in which at least one methylene group may be replaced by an oxygen atom, and n is an integer of 0 to 6.

Also preferred are (meth)acrylate compounds having the following general formulae (3) and (4).

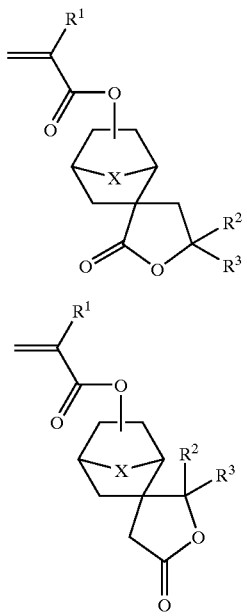

Herein, $R^1$, $R^2$, $R^3$, and X are as defined above.

Also preferred are (meth)acrylate compounds having the following general formula (5).

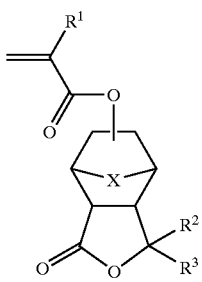

Herein, $R^1$, $R^2$, $R^3$, and X are as defined above.

In a second aspect, the invention provides a polymer comprising recurring units of the following general formula (6).

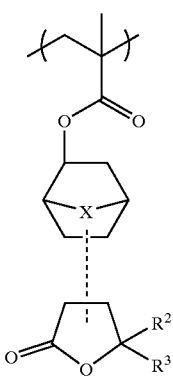

Herein, $R^1$, $R^2$, $R^3$, X and the broken line are as defined above.

The polymer may further include recurring units of the following general formula (7).

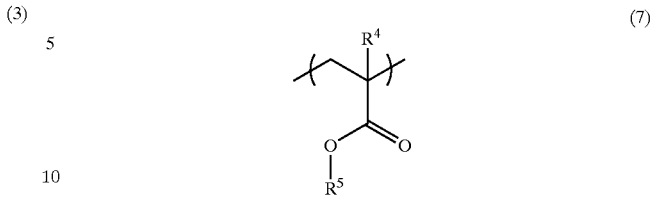

Herein, $R^4$ is hydrogen or methyl and $R^5$ is a tertiary alkyl group having 4 to 20 carbon atoms, said polymer having a weight average molecular weight of 2,000 to 100,000.

In a third aspect, the invention provides a photoresist composition comprising (A) the polymer defined above, (B) a photoacid generator, and (C) an organic solvent.

In a fourth aspect, the invention provides a process for forming a resist pattern comprising the steps of applying the photoresist composition onto a substrate to form a film; heat treating the film and then exposing it to high-energy radiation having a wavelength of less than 300 nm or electron beams through a photo mask; and optionally heat treating the exposed film and developing it with a developer.

DESCRIPTION OF THE PREFERRED EMBODIMENT

The (meth)acrylate compounds of the present invention have the general formula (1).

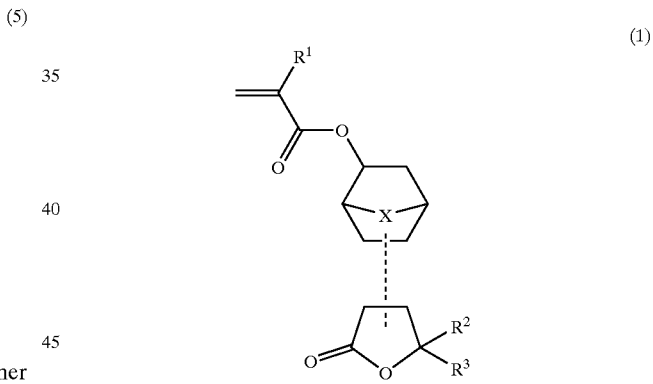

Herein, $R^1$ is hydrogen or methyl. $R^2$ and $R^3$ each are hydrogen or a straight, branched or cyclic alkyl group having 1 to 15 carbon atoms, preferably 1 to 8 carbon atoms, or $R^2$ and $R^3$, taken together, may form a ring and in that event, $R^2$ and $R^3$ together represent a straight, branched or cyclic alkylene group having 2 to 15 carbon atoms, preferably 2 to 5 carbon atoms. X is —CH$_2$—, —CH$_2$CH$_2$— or —O— or two separate —H. The broken line represents a single bond or divalent organic group that connects the norbornane ring, bicyclo[2.2.2]octane ring, 7-oxanorbornane ring or cyclohexane ring structure to the γ-butyrolactone ring structure, or a structure that shares one or two constituent carbon atoms between these ring structures.

The invention contemplates a norbornane ring structure when X is —CH$_2$—, a bicyclo[2.2.2]octane ring structure when X is —CH$_2$CH$_2$—, and a 7-oxanorbornane ring structure when X is —O—. And when X is two separate —H, a cyclohexane ring structure is formed as shown below.

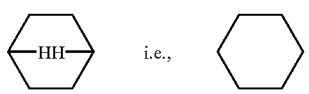 i.e.,

When the broken line represents a divalent organic group, alkylene groups of 1 to 6 carbon atoms and oxaalkylene groups having 2 to 5 carbon atoms are exemplary.

Of the (meth)acrylate compounds according to the invention, those of the following formula (2) are preferred as well as those of the following formulae (3), (4) and (5).

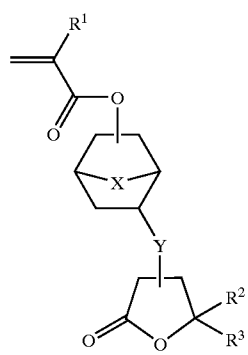

(2)

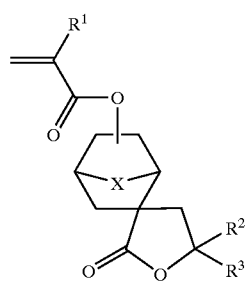

(3)

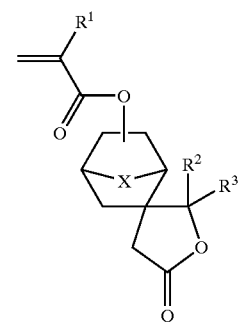

(4)

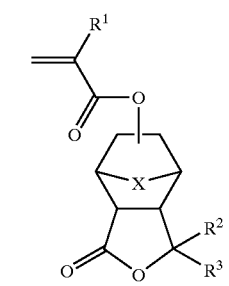

(5)

In formula (2), Y is —$(CH_2)_n$— in which one or more methylene groups may be replaced by one or more oxygen atoms, and n is an integer of 0 to 6. $R^1$, $R^2$, $R^3$ and X are as defined above.

Illustrative, non-limiting examples of the (meth)acrylate compounds according to the invention are given below.

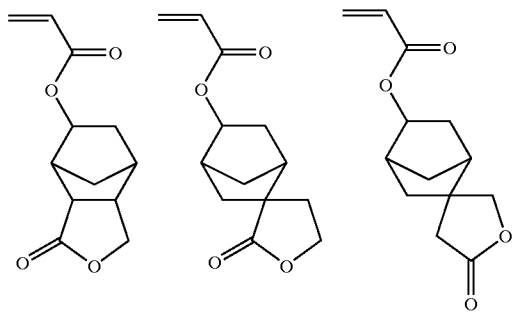

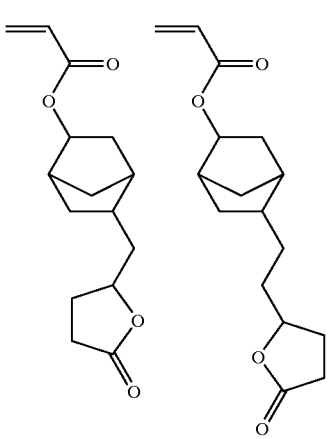

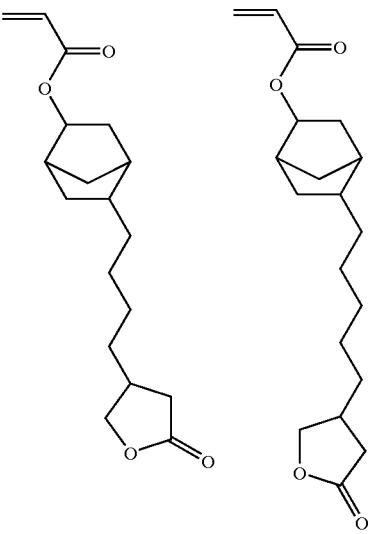

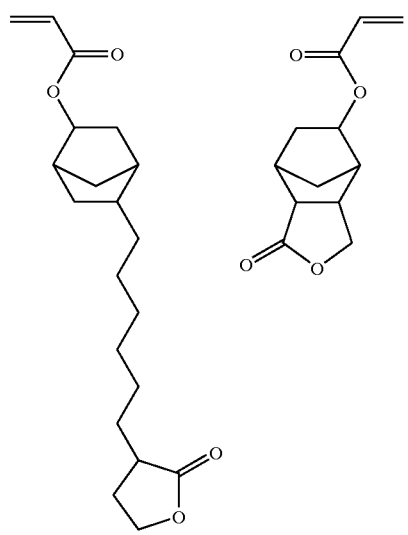
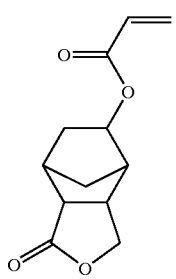
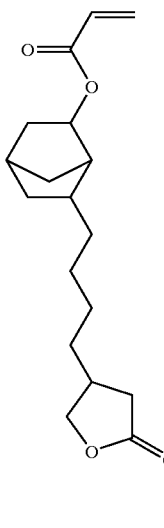
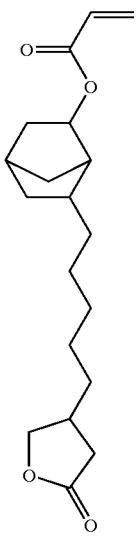
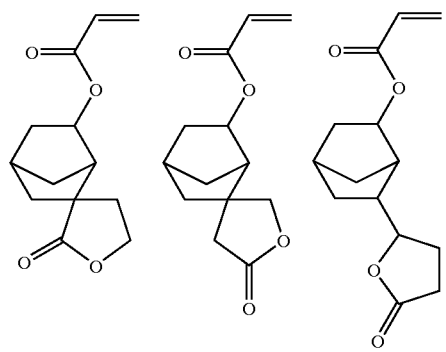
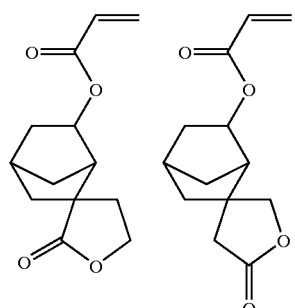
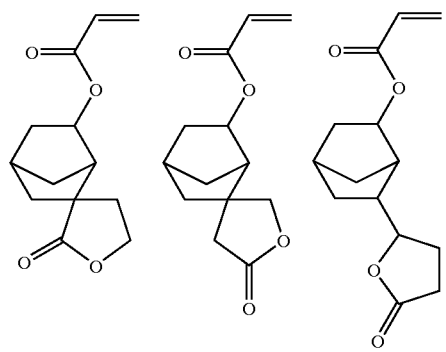
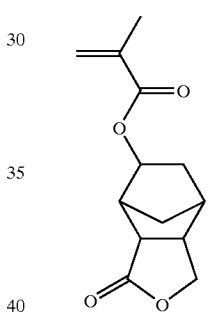
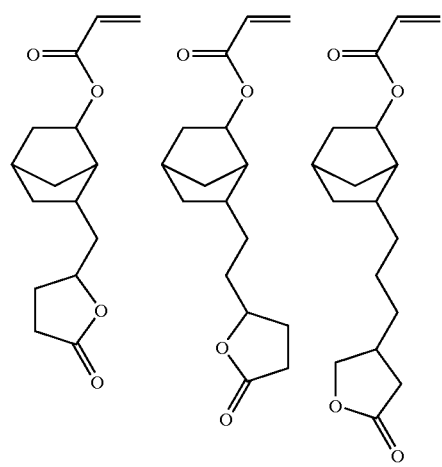
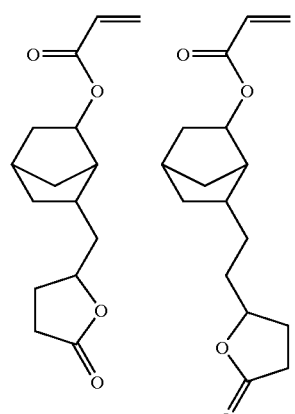
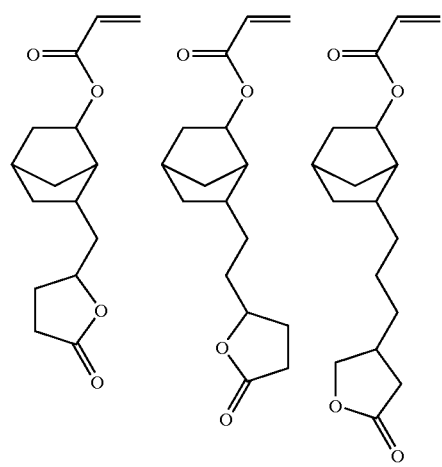
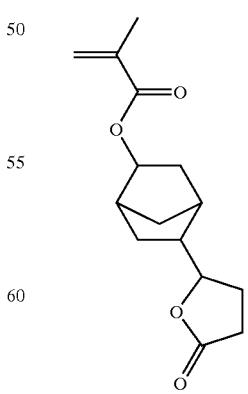
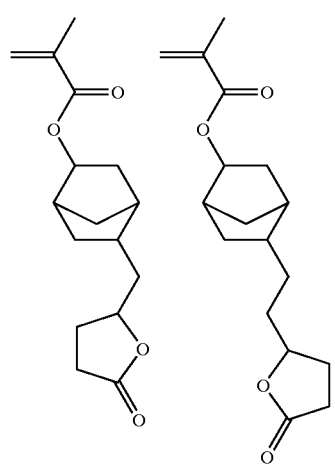
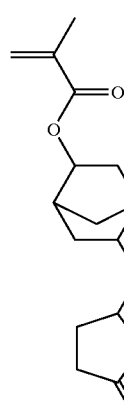
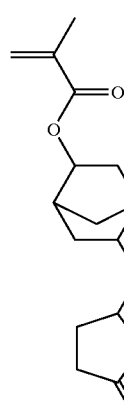

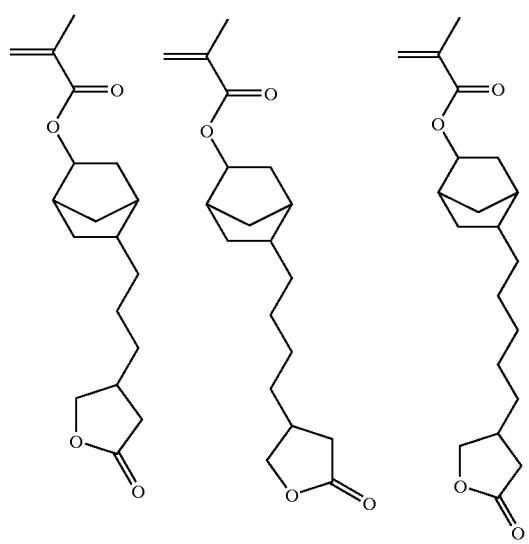
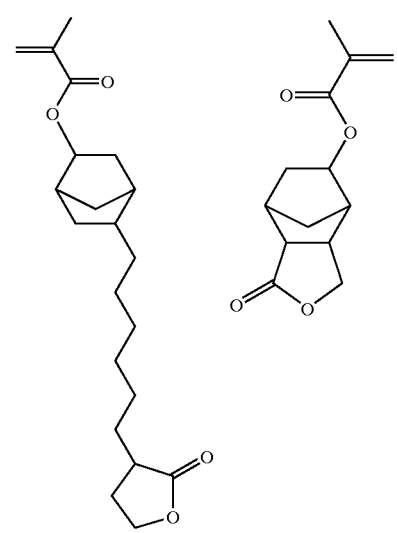
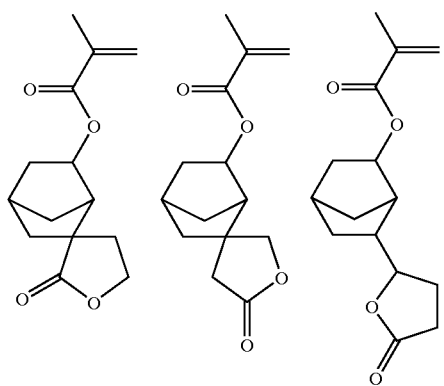
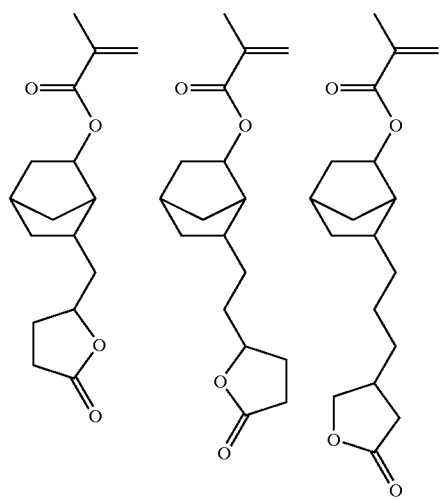
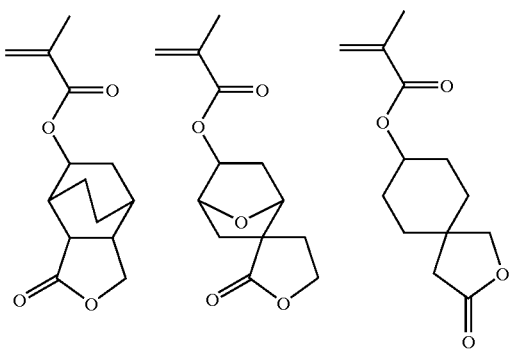

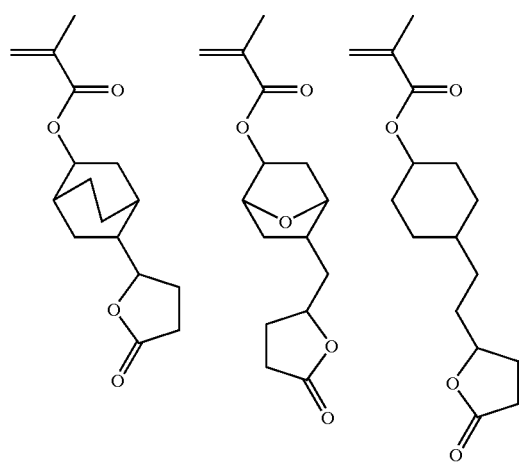
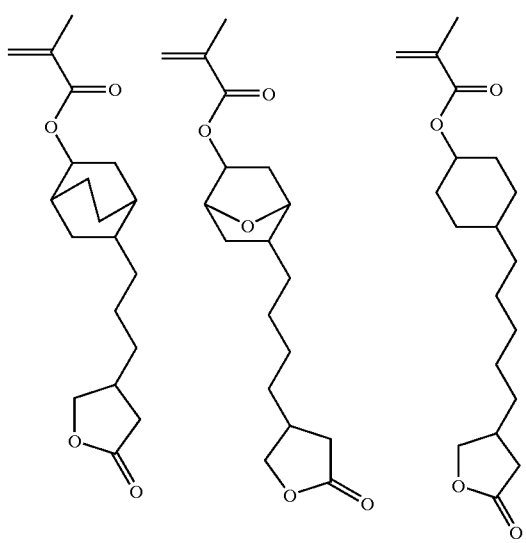
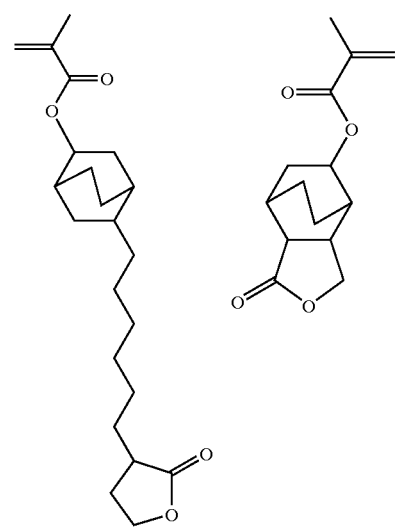
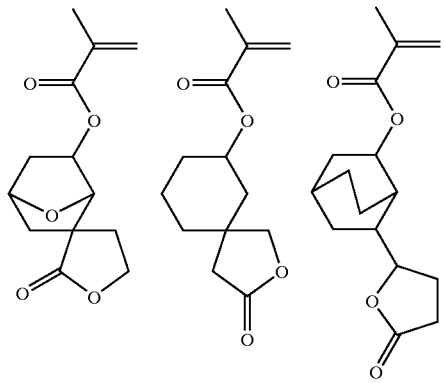
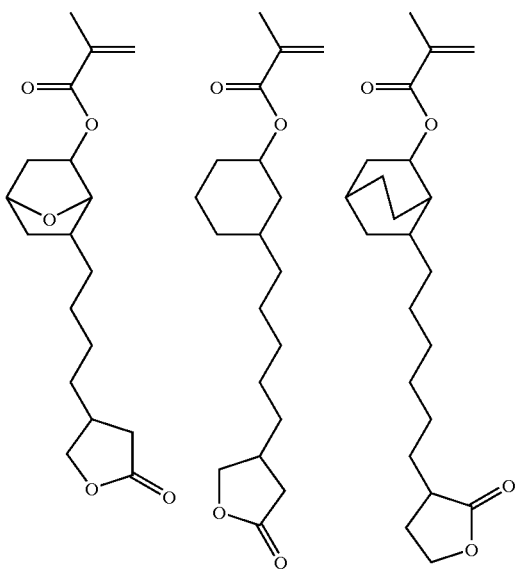

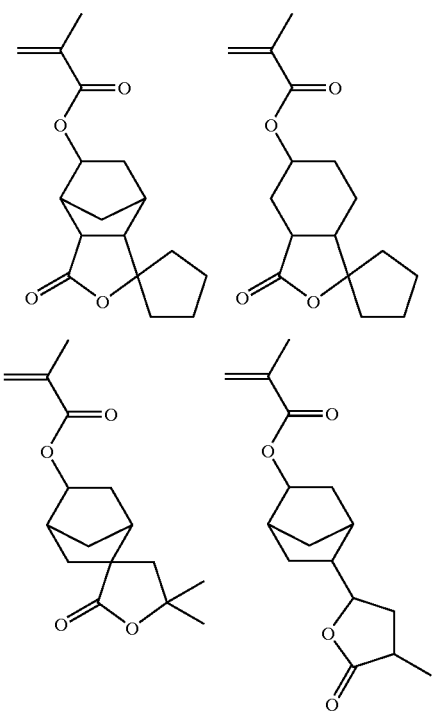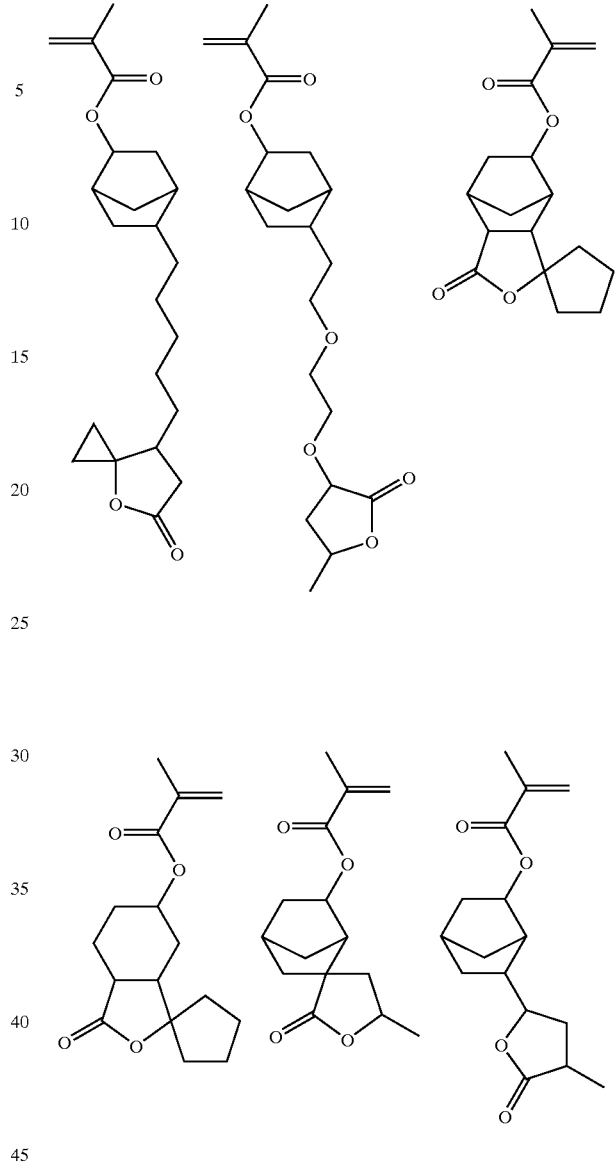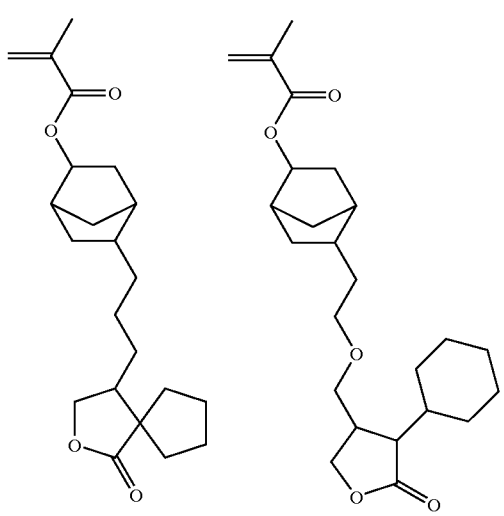

-continued

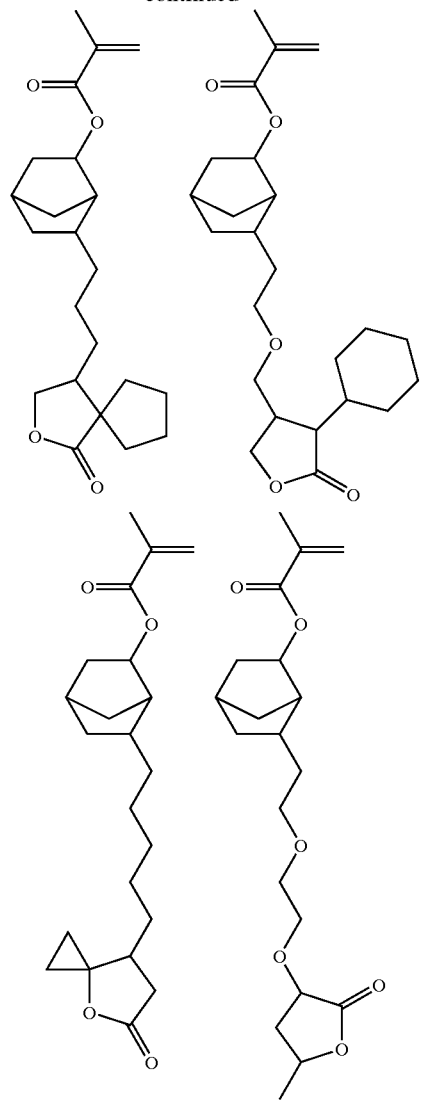

The (meth)acrylate compounds of the invention can be produced by the following method, for example, but the invention is not limited to this method.

The (meth)acrylate compound of formula (1) according to the invention can be obtained by esterifying a corresponding hydroxylactone compound of formula (8) (to form an acryloyl or methacryloyl compound) as shown below.

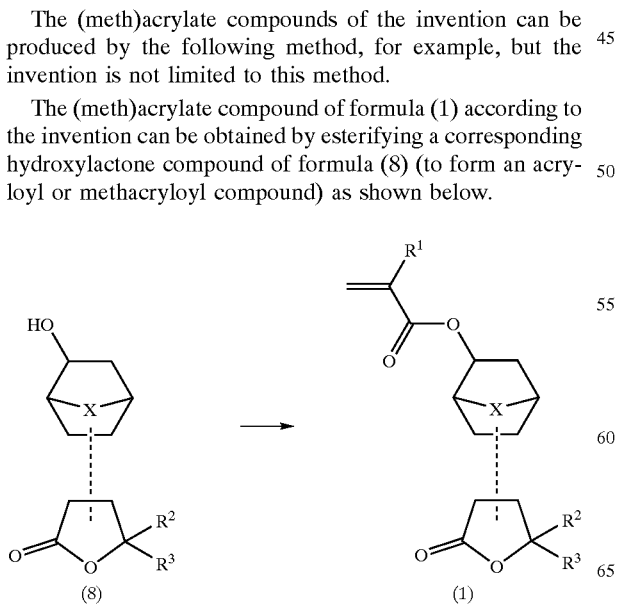

This reaction readily proceeds in a well-known manner. Preferably, reaction is carried out in a solvent such as methylene chloride, by successively or simultaneously adding the hydroxylactone compound (8), an esterifying agent such as (meth)acryloyl chloride, and a base such as triethylamine and optionally, cooling the reaction system.

The hydroxylactone compound (8) can be prepared by reducing a corresponding ketolactone compound (9) as shown below.

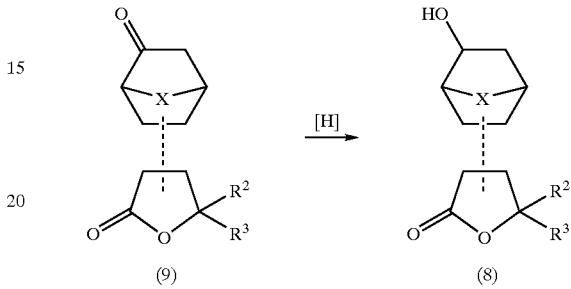

Herein, [H] represents a reducing agent.

For reduction of a keto group, a variety of reducing agents may be used. Examples of suitable reducing agents include metal hydrides such as borane, alkyl boranes, dialkyl boranes, dialkyl silanes, trialkyl silanes, sodium hydride, lithium hydride, potassium hydride, and calcium hydride; and complex hydrides and alkoxy or alkyl derivatives thereof such as sodium borohydride, lithium borohydride, potassium borohydride, calcium borohydride, sodium aluminum hydride, lithium aluminum hydride, sodium trimethoxyborohydride, lithium trimethoxyaluminum hydride, lithium diethoxyaluminum hydride, lithium tri-t-butoxyaluminum hydride, sodium bis(2-methoxyethoxy) aluminum hydride, and lithium triethylborohydride.

The hydroxylactone compound (8) can be also prepared from a corresponding olefin lactone compound (10) as shown below.

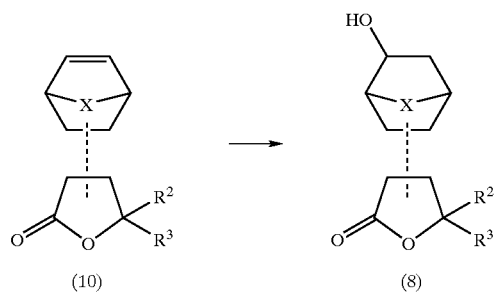

The olefin lactone compound (10) used as the starting reactant may be selected from among well-known compounds, the lactone compounds having an alicyclic structure (shown below) recited in U.S. Ser. No. 09/897,985, assigned to the same assignee as the present invention, and epoxy compounds having an alicyclic structure.

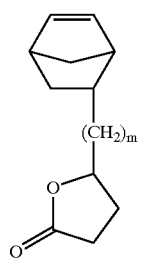

Herein, m is 1 to 8.

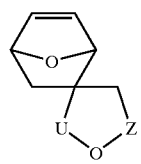

Herein, one of U and Z is —CR$^{O3}$R$^{O4}$— or —C(=O)—, and the other is CH$_2$. R$^{O3}$ and R$^{O4}$ each are independently hydrogen or a straight, branched or cyclic alkyl group having 1 to 6 carbon atoms, or R$^{O3}$ and R$^{O4}$, taken together, may form an aliphatic hydrocarbon ring with the carbon atom to which they are connected.

A first way of converting the olefin lactone compound (10) to the hydroxylactone compound (8) involves addition of an acid HY to the olefin lactone compound (10) and alkaline hydrolysis or alkaline solvolysis on the addition product.

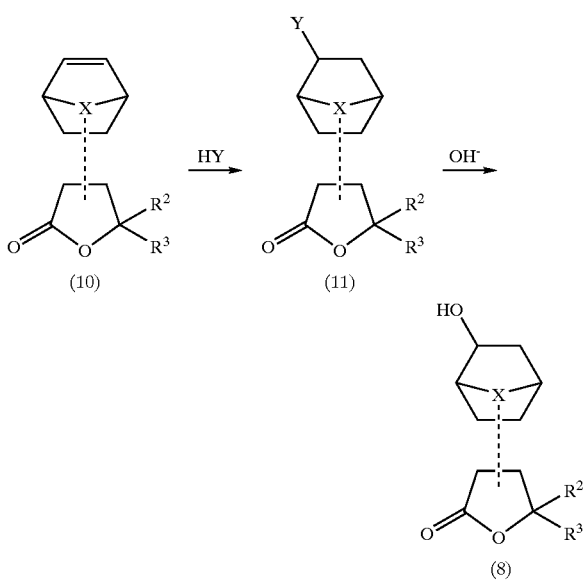

Herein HY stands for an acid and OH$^-$ stands for a base.

Examples of the acid HY used herein include inorganic acids such as hydrogen chloride, aqueous hydrochloric acid, hydrobromic acid, hydroiodic acid, and sulfuric acid, and organic acids such as formic acid, acetic acid, propionic acid, benzoic acid, chloroformic acid, chloroacetic acid, dichloroacetic acid, trichloroacetic acid, fluoroacetic acid, trifluoroacetic acid, and 3,3,3-trifluoropropionic acid. If acrylic or methacrylic acid can be used as the acid HY to be added to the olefin lactone compound (9), the (meth)acrylate compound (1) is directly synthesized. Examples of the base OH$^-$ include inorganic hydroxides such as sodium hydroxide, lithium hydroxide, potassium hydroxide, and barium hydroxide; inorganic carbonates such as sodium carbonate, sodium bicarbonate, lithium carbonate, and potassium carbonate; alkoxides such as sodium methoxide, sodium ethoxide, lithium methoxide, lithium ethoxide, lithium tert-butoxide, and potassium tert-butoxide; and organic bases such as diethylamine, triethylamine, tri-n-butylamine, and dimethylaniline.

A second way of converting the olefin lactone compound (10) to the hydroxylactone compound (8) involves epoxidation of the olefin lactone compound (10) and reductive cleavage of the resulting epoxide compound.

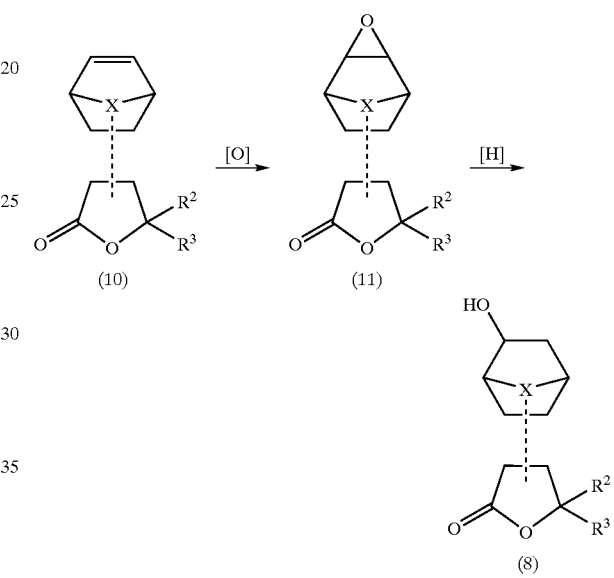

Herein [O] stands for an oxidizing agent and [H] stands for a reducing agent.

Examples of the oxidizing agent [O] used herein include peracids such as performic acid, peracetic acid, trifluoroperacetic acid, and m-chloroperbenzoic acid, and peroxides such as hydrogen peroxide, dimethyl dioxirane, and tert-butyl hydroperoxide. In the reaction using such an oxidizing agent, a metal or metal salt may be co-present as a catalyst. Examples of the reducing agent [H] include hydrogen, metal hydrides such as borane, alkyl boranes, dialkyl boranes, dialkyl silanes, trialkyl silanes, sodium hydride, lithium hydride, potassium hydride, and calcium hydride; and complex hydrides and alkoxy or alkyl derivatives thereof such as sodium borohydride, lithium borohydride, potassium borohydride, calcium borohydride, sodium aluminum hydride, lithium aluminum hydride, sodium trimethoxyborohydride, lithium trimethoxyaluminum hydride, lithium diethoxyaluminum hydride, lithium tri-t-butoxyaluminum hydride, sodium bis(2-methoxyethoxy) aluminum hydride, and lithium triethylborohydride. In the reaction using such a reducing agent, a metal or metal salt may be co-present as a catalyst.

A third way of converting the olefin lactone compound (10) to the hydroxylactone compound (8) is hydroboration-oxidation.

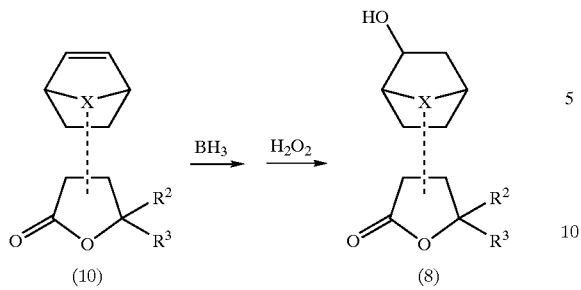

(10) → (8)

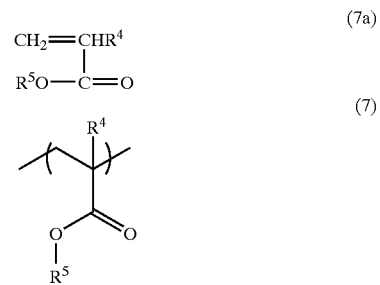

(7a), (7)

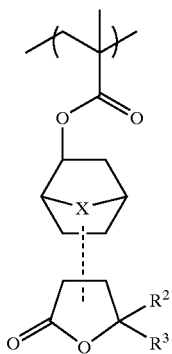

(6)

In general, once borane (BH$_3$) is added to the olefin lactone compound (10), it is oxidized with aqueous hydrogen peroxide under alkaline conditions for converting to the hydroxylactone compound (8). A variety of conditions well-known to hydroboration and oxidation may be used.

The present invention also provides a polymer or high molecular weight compound obtained using the inventive (meth)acrylate compound as a monomer. Therefore, the polymer includes recurring units of the following formula (6) originating from the (meth)acrylate compound.

In the resist polymer synthesized using the (meth)acrylate compound as a monomer, the butyrolactone moiety regarded as a polar group can be positioned at a desired site from the polymer backbone by selecting the presence or absence of a linker such as an alkylene group and properly selecting the length of the linker if any, so that satisfactory substrate adhesion is accomplished. By properly selecting the type and length of the linker in the (meth)acrylate compound used as the monomer, the hydrophobicity of the overall polymer can be adjusted. That is, the dissolution properties of the polymer are controllable.

Preferably, the polymer of the invention is prepared using another copolymerizable monomer as well as the (meth)acrylate compound. The compounds which can be copolymerized with the (meth)acrylate compound of the invention include a variety of compounds having a polymerizable carbon-carbon double bond. Illustrative examples are α,β-unsaturated carboxylic acids such as (meth)acrylic acid, α,β-unsaturated carboxylic esters such as (meth)acrylates, crotonates, and maleates, α,β-unsaturated nitrites such as acrylonitrile, α,β-unsaturated lactones such as 5,6-dihydro-2H-pyran-2-one, maleic anhydride, itaconic anhydride, maleimides, norbornene derivatives, tetracyclo[4.4.0.1$^{2,5}$.1$^{7,10}$]dodecene derivatives, allyl ethers, vinyl ethers, and vinyl esters.

In one preferred embodiment, recurring units of the following formula (7) can be introduced in the polymer using a monomer of the following formula (7a).

In formula (7a) and (7), R$^4$ is hydrogen or methyl, and R$^5$ is a tertiary alkyl group having 4 to 20 carbon atoms. Examples of suitable tertiary alkyl groups represented by R$^5$ include t-butyl, t-pentyl, 1-ethyl-1-methylpropyl, triethylcarbinyl, 1-methylcyclopentyl, 1-ethylcyclopentyl, 1-cyclopentylcyclopentyl, 1-cyclohexylcyclopentyl, 1-methylcyclohexyl, 1-ethylcyclohexyl, 1-cyclopentylcyclohexyl, 1-cyclohexylcyclohexyl, 2-methyl-2-norbornyl, 2-ethyl-2-norbornyl, 8-methyl-8-tricyclo[5.2.1.0$^{2,6}$]decyl, 8-ethyl-8-tricyclo[5.2.1.0$^{2,6}$]decyl, 2-methyl-2-adamantyl, 2-ethyl-2-adamantyl, and 1-adamantyl-1-methylethyl, but are not limited thereto.

Polymerization of the inventive (meth)acrylate compound with the other polymerizable compound may be carried out by any conventional technique such as radical, anionic and cationic polymerization techniques.

The polymer of the invention is preferably composed of 1 to 90 mol %, especially 5 to 80 mol % of units of formula (6) and 5 to 90 mol %, especially 10 to 80 mol % of units of formula (7).

The polymer of the invention serving as a resist base polymer should preferably have a weight average molecular weight (Mw) of about 2,000 to about 100,000. With a Mw of less than 2,000, film formation and resolution may be poor whereas a Mw of more than 100,000 can compromise resolution.

Advantageously, the polymer of the invention is used in a photoresist composition, especially a chemically amplified positive resist composition. The photoresist composition is typically comprised of (A) the above-described polymer as a base resin, (B) a photoacid generator, and (C) an organic solvent.

The photoacid generator (B) may be any compound capable of generating an acid upon exposure to high energy radiation having a wavelength of less than 300 nm or electron beams as long as a resist composition comprising the photoacid generator, the inventive polymer and a solvent can be a homogeneous solution which is effectively applicable to form a uniform film. Such photoacid generators may be used alone or in admixture of any.

Examples of suitable photoacid generators which can be used herein include triphenylsulfonium salt derivatives such as triphenylsulfonium trifluoromethanesulfonate, diphenyliodonium salt derivatives such as di-p-t-butyliodonium trifluoromethanesulfonate, other onium salts, alkylsulfonic acids, dialkylsulfonyldiazomethanes, disulfones, and sulfonimides. An appropriate amount of the photoacid generator is 0.2 to 50 parts, especially 0.5 to 40 parts by weight per 100 parts by weight of the entire base polymer. Less than 0.2 part of the photoacid generator may generate a less amount of acid upon exposure, resulting in a low sensitivity and resolution. More than 50 parts of the photoacid generator can compromise the transmittance of the resist film, detracting from resolution.

The organic solvent (C) may be any organic solvent in which the photoacid generator, base polymer and other components are dissolvable. Illustrative, non-limiting, examples of the organic solvent include ketones such as cyclohexanone; alcohols such as 1-methoxy-2-propanol and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate, propylene glycol monoethyl ether acetate, ethyl lactate, butyl acetate, methyl 3-methoxypropionate, and ethyl 3-ethoxypropionate; and lactones such as γ-butyrolactone. These solvents may be used alone or in combinations of two or more thereof. Of the above organic solvents, it is recommended to use diethylene glycol dimethyl ether and 1-ethoxy-2-propanol because the photoacid generator is most soluble therein, propylene glycol monomethyl ether acetate because it is a safe solvent, or a mixture thereof.

While the photoresist composition of the invention is basically composed of the inventive polymer, the photoacid generator, and the organic solvent as described above, it may further include any well-known components such as dissolution inhibitors, acidic compounds, basic compounds, stabilizers, dyes, and surfactants, if necessary.

Using the resist composition, a pattern can be formed by a conventional procedure. Typically, a resist pattern is formed by applying the photoresist composition onto a substrate, heat treating the film, exposing it to high energy radiation having a wavelength of less than 300 nm or an electron beam through a photomask, optionally heat treating the exposed film, and developing it with a developer.

EXAMPLE

Examples of the invention are given below by way of illustration and not by way of limitation.

Example 1
Synthesis of a Mixture of 8-methacryloyloxy-4-oxatricyclo-[5.2.2.0$^{2,6}$]undecan-3-one and 9-methacryloyloxy-4-oxatricyclo[5.2.2.0$^{2,6}$]undecan-3-one (Monomer 1)

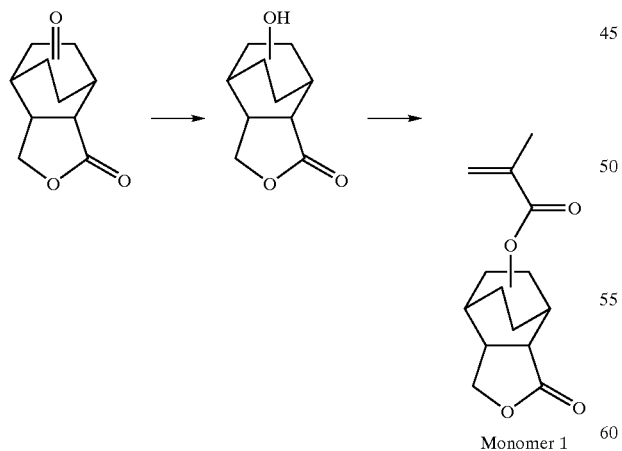

Monomer 1

Example 1-1
Reduction

With stirring at room temperature, a solution of 57.7 g of an approximately 1:1 mixture of ketolactone compounds, 4-oxatricyclo[5.2.2.0$^{2,6}$]undeca-3,8-dione and 4-oxatricyclo-[5.2.2.0$^{2,6}$]undeca-3,9-dione in 100 ml of tetrahydrofuran was added dropwise to a solution of 7.0 g of sodium borohydride in 50 ml of water. After 3 hours of stirring at room temperature, the reaction mixture was poured into dilute hydrochloric acid and extracted with ethyl acetate. The ethyl acetate solution was washed with an aqueous saturated sodium bicarbonate solution and an aqueous saturated sodium chloride solution, dried over magnesium sulfate, and concentrated in vacuo, obtaining 58.3 g of a mixture of crude hydroxylactone compounds, 8-hydroxy-4-oxatricyclo[5.2.2.0$^{2,6}$]undecan-3-one and 9-hydroxy-4-oxatricyclo[5.2.2.0$^{2,6}$]undecan-3-one.

Example 1-2
Methacryloylation

With stirring at 5–10° C., 35 ml of methacryloyl chloride was added dropwise to a mixture of 58.3 g of the crude hydroxylactone compounds obtained in Example 1-1, 60 ml of triethylamine, 100 mg of 4-dimethylaminopyridine and 200 ml of methylene chloride. After 5 hours of stirring at 5–10° C., the reaction mixture was poured into ice water and extracted with ethyl acetate. The ethyl acetate solution was washed with dilute hydrochloric acid, an aqueous saturated sodium bicarbonate solution and an aqueous saturated sodium chloride solution, dried over magnesium sulfate, and concentrated in vacuo. Purification by silica gel column chromatography gave 63.1 g of target methacrylate compounds (Monomer 1). Overall yield 79%.

IR (liquid film) of Monomer 1 (mixture of regioisomers): ν=2945, 2873, 1765, 1713, 1320, 1296, 1173, 945 cm$^{-1}$
$^1$H-NMR (300 MHz, CDCl$_3$) of Monomer 1 (mixture of regioisomers): δ=1.40–2.80 (12H, m), 4.20–4.54 (2H, m), 4.85–5.06 (1H, m), 5.54–5.06 (1H, m), 5.54–5.60 (1H, m), 6.05–6.14 (1H, m) ppm.

Example 2
Synthesis of a Mixture of spiro[cyclopentane-1,5'-(8'-methacryloyloxy-4'-oxatricyclo[5.2.1.0$^{2,6}$]decan-3'-one)] and spiro[cyclopentane-1,5'-(9'-methacryloyloxy-4'-oxatricyclo-[5.2.1.0$^{2,6}$]decan-3'-one)] (Monomer 2)

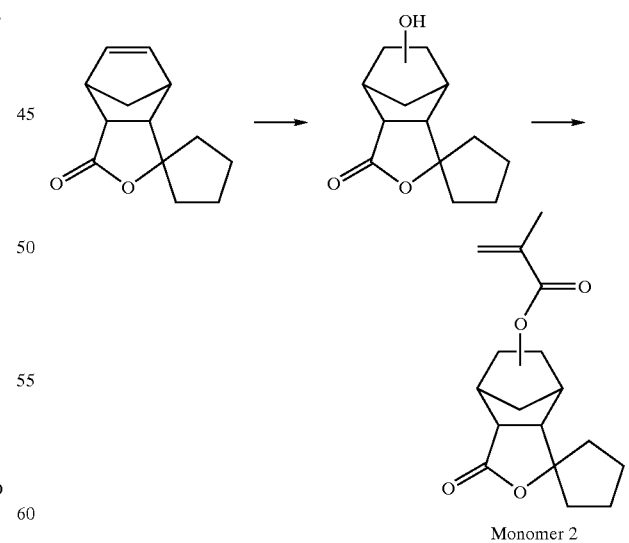

Monomer 2

Example 2-1
Hydroboration-oxidation

With stirring at 5–15° C., a tetrahydrofuran solution of 1.0M borane was added dropwise to a solution of 24.5 g of spiro[cyclopentane-1,5'-(4'-oxatricyclo[5.2.1.0$^{2,6}$]dec-8'-en-3'-one)] in 100 ml of tetrahydrofuran. After one hour of stirring at the temperature, 14 ml of water and then 63 ml of an aqueous 2.5N sodium hydroxide solution was added. With stirring under ice cooling, 48 ml of 35% aqueous hydrogen peroxide was slowly added dropwise to the mixture so as to keep the reaction temperature below 30° C. The reaction mixture was stirred for one hour at 40° C., poured into ice water, and extracted with ethyl acetate. The ethyl acetate solution was washed with an aqueous saturated sodium chloride solution and concentrated in vacuo, obtaining 23.3 g of a mixture of crude hydroxylactone compounds, spiro[cyclopentane-1,5'-(8'-hydroxy-4'-oxatricyclo-[5.2.1.0$^{2,6}$]decan-3'-one)] and spiro[cyclopentane-1,5'-(9'-hydroxy-4'-oxatricyclo[5.2.1.0$^{2,6}$]decan-3'-one)].

Example 2-2

Methacryloylation

Aside from using 23.3 g of the crude hydroxylactone compounds obtained in Example 2-1 instead of the crude hydroxylactone compounds of Example 1-1 used in Example 1-2, methacryloylation was carried out by the same procedure as in Example 1-2. Purification by silica gel column chromatography gave 24.6 g of target methacrylate compounds (Monomer 2). Overall yield 71%.

IR (liquid film) of Monomer 2 (mixture of stereo- and regioisomers): ν=2964, 2877, 1761, 1713, 1325, 1302, 1169, 978 cm$^{-1}$ $^1$H-NMR (300 MHz, CDCl$_3$) of Monomer 2 (mixture of stereo- and regioisomers): δ=1.35–3.30 (19H, m), 4.80–5.16 (1H, m), 5.40–5.65 (1H, m), 6.00–6.11 (1H, m) ppm.

$^{13}$C-NMR (75 MHz, CDCl$_3$, peaks due to two major isomers) of Monomer 2 (mixture of stereo- and regioisomers): 18.17, 18.17, 23.41, 23.58, 24.21, 24.55, 32.89, 33.56, 34.07, 35.29, 38.61, 38.72, 38.94, 39.28, 43.64, 43.96, 44.53, 45.48, 46.05, 47.21, 50.36, 51.09, 72.85, 73.61, 93.77, 93.97, 125.11, 125.44, 136.28, 136.44, 166.25, 166.96, 176.41, 177.24 ppm Example 3

Synthesis of a Mixture of 1',6'-cis-spiro[cyclopentane-1,9'-(3'-methacryloyloxy-8'-oxabicyclo[4.3.0]nonan-7'-one)] and 1',6'-cis-spiro[cyclopentane-1,9'-(4'-methacryloyloxy-8'-oxabicyclo[4.3.0]nonan-7'-one)] (Monomer 3)

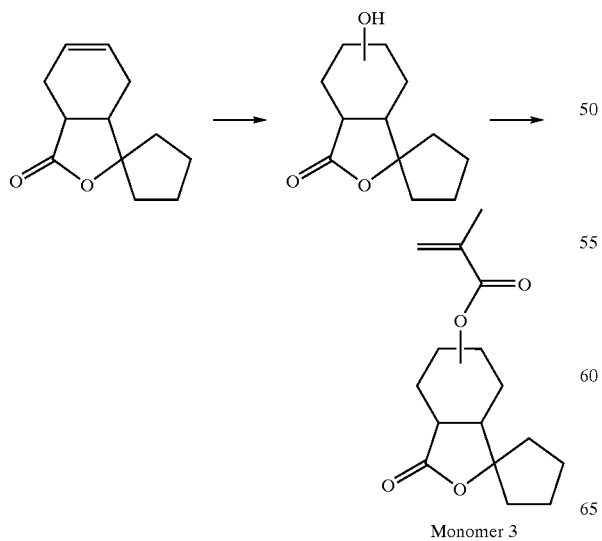

Monomer 3

Example 3-1

Hydroboration-oxidation

Aside from using 48.1 g of 1',6'-cis-spiro-[cyclopentane-1,9'-(8'-oxabicyclo[4.3.0]non-3'-en-7'-one)] instead of the spiro[cyclopentane-1,5'-(4'-oxatricyclo-[5.2.1.0$^{2,6}$]dec-8'-en-3'-one)] in Example 2-1, hydroboration-oxidation was carried out by the same procedure as in Example 2-1. There was obtained 52.2 g of a mixture of crude hydroxylactone compounds, 1',6'-cis-spiro-[cyclopentane-1,9'-(3'-hydroxy-8'-oxabicyclo[4.3.0]nonan-7'-one)] and 1',6'-cis-spiro [cyclopentane-1,9'-(4'-hydroxy-8'-oxabicyclo[4.3.0]nonan-7'-one)].

Example 3-2

Methacryloylation

Aside from using 52.2 g of the crude hydroxylactone compounds obtained in Example 3-1 instead of the crude hydroxylactone compounds of Example 1-1 used in Example 1-2, methacryloylation was carried out by the same procedure as in Example 1-2. Purification by silica gel column chromatography gave 52.2 g of target methacrylate compounds (Monomer 3). Overall yield 75%.

IR (liquid film) of Monomer 3 (mixture of regioisomers): ν=2958, 2866, 1765, 1707, 1633, 1346, 1298, 1191, 1161, 964, 941 cm$^{-1}$ $^1$H-NMR (300 MHz, CDCl$_3$, peaks due to major isomers) of Monomer 3 (mixture of regioisomers): δ=1.20–2.50 (18H, m), 3.03–3.12 (1H, m), 4.60–4.70 (1H, m), 5.48–5.56 (1H, m), 6.02–6.12 (1H, m) ppm $^{13}$C-NMR (300 MHz, CDCl$_3$, peaks due to major isomers) of Monomer 3 (mixture of regioisomers): δ=18.14, 23.31, 23.34, 23.45, 28.08, 29.13, 33.22, 37.66, 41.57, 42.24, 69.89, 95.48, 125.11, 136.40, 166.34, 176.62 ppm Example 4

Synthesis of a Mixture of spiro[5-methacryloyloxy-norbornane-2,3'-tetrahydrofuran-2-one], spiro[6-methacryloyloxynorbornane-2,3'-tetrahydrofuran-2-one], spiro[5-methacryloyloxynorbornane-2,4'-tetrahydrofuran-2-one], and spiro[6-methacryloyloxynorbornane-2,4'-tetrahydrofuran-2-one] (Monomer 4)

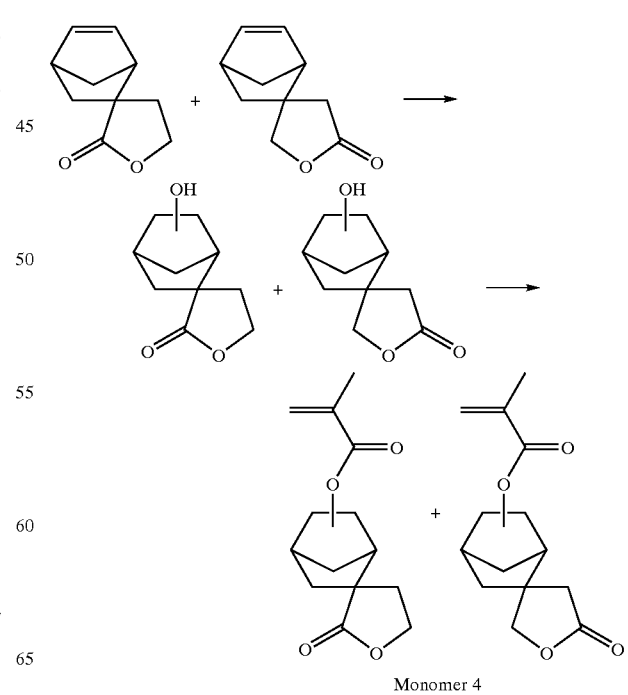

Monomer 4

Example 4-1
Addition of Formic Acid-methanolysis

To 164 g of a mixture of spiro[5-norbornene-2,3'-tetrahydrofuran-2-one] and spiro[5-norbornene-2,4'-tetrahydrofuran-2-one] was added 800 g of formic acid. This was stirred at 100° C. for 10 hours. After cooling, the reaction mixture was concentrated in vacuo to remove the most of formic acid. The residue was dissolved in 1,500 ml of toluene. The toluene solution was washed with an aqueous saturated sodium carbonate solution, dried over magnesium sulfate, and concentrated in vacuo. To the residue were added 1,000 ml of methanol and 5 g of potassium carbonate. The resulting mixture was stirred at room temperature for 10 hours. The reaction mixture was concentrated in vacuo to remove the most of methanol. The residue was dissolved in 1,000 ml of ethyl acetate. The ethyl acetate solution was washed with 20% hydrochloric acid, then with an aqueous saturated sodium chloride solution, dried over magnesium sulfate, and concentrated in vacuo, obtaining 164 g of a mixture of crude hydroxylactone compounds, spiro[5-hydroxynorbornane-2,3'-tetrahydrofuran-2-one], spiro[6-hydroxynorbornane-2,3'-tetrahydrofuran-2-one], spiro[5-hydroxynorbornane-2,4'-tetrahydrofuran-2-one], and spiro[6-hydroxynorbornane-2,4'-tetrahydrofuran-2-one].

Example 4-2
Methacryloylation

Aside from using 82 g of the crude hydroxylactone compounds obtained in Example 4-1 instead of the crude hydroxylactone compounds of Example 1-1 used in Example 1-2, methacryloylation was carried out by the same procedure as in Example 1-2. Purification by silica gel column chromatography gave 89 g of target methacrylate compounds (Monomer 4). Overall yield 71%.

IR (liquid film) of Monomer 4 (mixture of stereo- and regioisomers): ν=2966, 2879, 1784, 1705, 1632, 1452, 1414, 1381, 1331, 1308, 1290, 1178, 1022 cm$^{-1}$ $^{13}$C-NMR (75 MHz, CDCl$_3$, peaks due to two major isomers) of Monomer 4 (mixture of stereo- and regioisomers): 18.18, 18.18, 33.71, 34.72, 34.93, 35.49, 37.86, 39.09, 39.88, 42.20, 42.39, 43.33, 43.64, 44.12, 45.70, 45.95, 75.76, 75.89, 75.91, 80.06, 125.39, 125.42, 136.33, 136.34, 166.84, 166.84, 176.18, 176.31 ppm

Example 5
Synthesis of a Mixture of spiro[5-acryloyloxynorbornane-2,3'-tetrahydrofuran-2-one], spiro[6-acryloyloxynorbornane-2,3'-tetrahydrofuran-2-one], spiro[5-acryloyloxynorbornane-2,4'-tetrahydrofuran-2-one], and spiro[6-acryloyloxynorbornane-2,4'-tetrahydrofuran-2-one] (Monomer 5)

Example 5-1
Acryloylation

With stirring at 5–10° C., 56 ml of acryloyl chloride was added dropwise to a mixture of 82 g of the crude hydroxylactone compounds obtained in Example 4-1, 100 ml of triethylamine, 200 mg of 4-dimethylaminopyridine and 400 ml of methylene chloride. After 5 hours of stirring at 5–10° C., the reaction mixture was poured into ice water and extracted with ethyl acetate. The ethyl acetate solution was washed with dilute hydrochloric acid, an aqueous saturated sodium bicarbonate solution and an aqueous saturated sodium chloride solution, dried over magnesium sulfate, and concentrated in vacuo. Purification by silica gel column chromatography gave 69.4 g of target acrylate compounds (Monomer 5). Overall yield 59%.

IR (liquid film) of Monomer 5 (mixture of stereo- and regioisomers): ν=2964, 2885, 1780, 1714, 1633, 1410, 1306, 1294, 1279, 1192, 1014, 984 cm$^{-1}$ $^1$H-NMR (300 MHz, CDCl$_3$) of Monomer 5 (mixture of stereo- and regioisomers): δ=1.20–1.55 (3H, m), 1.60–1.80 (2H, m), 1.90–2.08 (1H, m), 2.10–2.22 (1H, m), 2.30–2.40 (1H, m), 2.40–2.45 (1H, m), 2.45–2.60 (1H, m), 3.95–4.50 (2H, m), 4.60–4.90 (1H, m), 5.75–5.85 (1H, m), 6.00–6.15 (1H, m), 6.30–6.40 (1H, m) ppm

Example 6
Synthesis of a Mixture of γ-(5-methacryloyloxynorbornan-2-yl)ethyl-γ-butyrolactone and γ-(6-methacryloyloxynorbornan-2-yl)ethyl-γ-butyrolactone (Monomer 6)

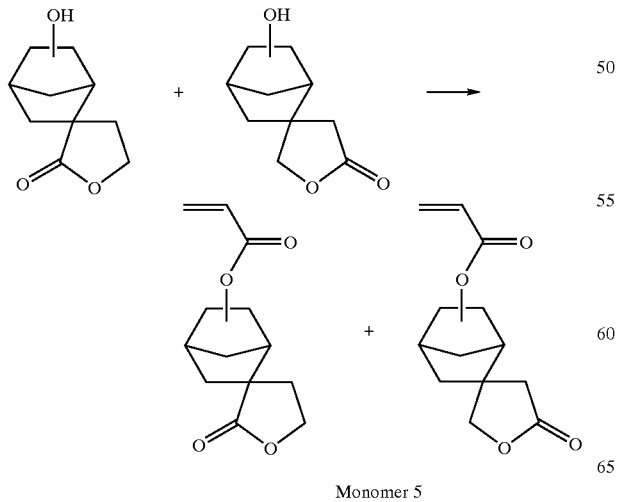

Monomer 5

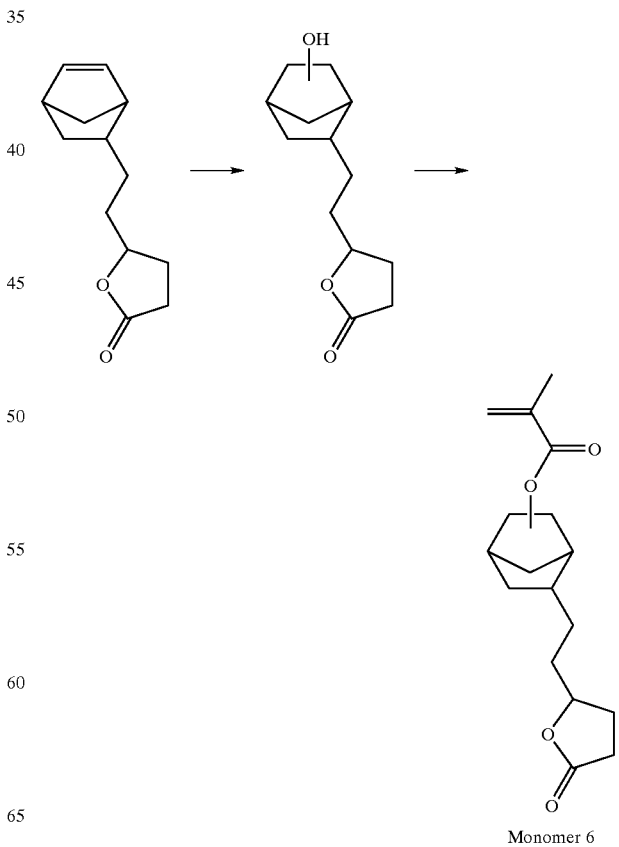

Monomer 6

Example 6-1
Addition of Formic Acid-methanolysis

Aside from using 20.6 g of γ-(5-norbornen-2-yl)ethyl-γ-butyrolactone (mixture of endo-and exo-isomers) instead of the mixture of spiro[5-norbornene-2,3'-tetrahydrofuran-2-one] and spiro[5-norbornene-2,4'-tetrahydrofuran-2-one] used in Example 4-1, addition of formic acid-methanolysis was carried out by the same procedure as in Example 4-1. There was obtained 22.4 g of a mixture of crude hydroxylactone compounds, γ-(5-hydroxynorbornan-2-yl)ethyl-γ-butyrolactone and γ-(6-hydroxynorbornan-2-yl)ethyl-γ-butyrolactone.

Example 6-2
Methacryloylation

Aside from using 22.4 g of the crude hydroxylactone compounds obtained in Example 6-1 instead of the crude hydroxylactone compounds of Example 1-1 used in Example 1-2, methacryloylation was carried out by the same procedure as in Example 1-2. Purification by silica gel column chromatography gave 24.3 g of target methacrylate compounds (Monomer 6). Overall yield 83%.

IR (liquid film) of Monomer 6 (mixture of stereo- and regioisomers): ν=2954, 2873, 1776, 1713, 1635, 1454, 1325, 1296, 1174, 1012 $cm^{-1}$ $^1$H-NMR (300 MHz, $CDCl_3$) of Monomer 6 (mixture of stereo- and regioisomers): δ=1.00–2.40 (18H, m), 2.45–2.55 (1H, m), 4.35–4.70 (2H, m), 5.47–5.50 (1H, m), 6.00–6.70 (1H, m) ppm

Example 7
Synthesis of the Following Polymer (Polymer 1)

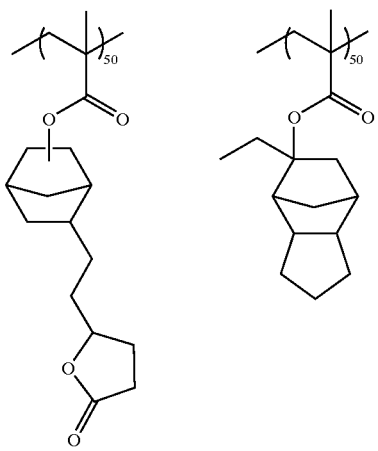

Polymer 1

In a nitrogen atmosphere, a mixture of 14.6 g of the methacrylate compound obtained in Example 6, 12.4 g of 8-ethyl-8-tricyclo[$5.2.1.0^{2,6}$]decyl methacrylate, 60 mg of N,N'-azobisisobutyronitrile, and 100 ml of tetrahydrofuran was heated and stirred at 60° C. for 20 hours. After cooling, the reaction mixture was added dropwise to 2 liters of methanol under vigorous stirring. The precipitate which settled down was collected by filtration. The solids were washed with methanol and dried in vacuo, obtaining 14.9 g (yield 55%) of the polymer. An integration ratio calculated from its $^1$H-NMR spectrum indicated a copolymerization ratio of 50:50. GPC analysis using a polystyrene standard indicated a weight average molecular weight (Mw) of 10,200 and a polydispersity index (Mw/Mn) of 1.78.

Example 8
Resist Pattern Formation Using Polymer

Using the polymer obtained in Example 7, a resist material was prepared. Its composition was:

(A) 80 parts by weight of the polymer of Example 7 as a base polymer, (B) 1.0 part by weight of triphenylsulfonium trifluoromethanesulfonate as a photoacid generator, (C) 480 parts by weight of propylene glycol monomethyl ether acetate as a solvent, and (D) 0.08 part by weight of tributylamine as a basic compound.

This was passed through a Teflon® filter having a pore diameter of 0.2 μm. The resist solution was spin coated on a silicon wafer having hexamethyldisilazane sprayed thereon at 90° C. for 40 seconds and heat treated at 110° C. for 90 seconds, forming a resist film of 500 nm thick. The resist film was exposed to ArF excimer laser light, heat treated at 110° C. for 90 seconds, and dipped in a 2.38% tetramethylammonium hydroxide aqueous solution for 60 seconds for development, thereby forming a 1:1 line-and-space pattern. The wafer as developed was observed under top-down SEM. Patterns down to a line width of 0.17 μm were left unstrapped and hence, resolved. This demonstrates that the photoresist material of the invention has improved substrate adhesion and resolution.

Example 9
Evaluation of Transparency of Polymer

The polymer obtained in Example 7, 1.0 g, was dissolved in 6.0 g of cyclohexanone, which was passed through a Teflon filter having a pore diameter of 0.2 μm. The solution was spin coated on a quartz substrate and heat treated at 90° C. for 60 seconds, forming a thin film of 500 nm thick. The thin film was measured for transmittance at 193 nm using a UV-visible spectrophotometer, finding a transmittance of 80% per 500 nm. This result demonstrates that the polymer of the invention has a sufficient transparency as the photoresist base polymer for excimer laser photolithography.

There have been described (meth)acrylate compounds having a lactone structure which are very advantageous in improving the resolution of photoresists. The polymers obtained therefrom have improved transparency, especially at the exposure wavelength of an excimer laser. Resist compositions comprising the inventive polymers lend themselves to micropatterning with electron beams or deep-UV rays since they are sensitive to high-energy radiation and have a high resolution. Especially because of firm adhesion to the substrate, finely defined patterns having sidewalls perpendicular to the substrate can easily be formed. The resist compositions are thus suitable as micropatterning material for VLSI fabrication.

Japanese Patent Application No. 2001-179614 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

What is claimed is:

1. A (meth)acrylate compound having the following general formula (1):

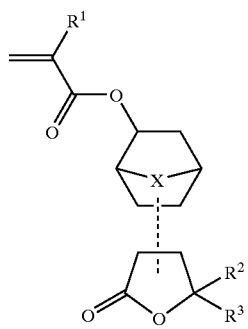

wherein $R^1$ is hydrogen or methyl, $R^2$ and $R^3$ each are hydrogen or a straight, branched or cyclic alkyl group having 1 to 15 carbon atoms, or $R^2$ and $R^3$, taken together, may form a ring and in that event, $R^2$ and $R^3$ together represent a straight, branched or cyclic alkylene group having 2 to 15 carbon atoms, X is —$CH_2$—, —$CH_2CH_2$— or —O— or two separate —H, with the proviso that $R^2$ and $R^3$ are not simultaneously hydrogen if X is —$CH_2$, and the broken line represents a single bond or divalent organic group that connects the norbornane ring, bicyclo[2.2.2]octane ring, 7-oxanorbornane ring or cyclohexane ring structure to the γ-butyrolactone ring structure, or a structure that shares one or two constituent carbon atoms between these ring structures.

2. A (meth)acrylate compound having the following general formula (2):

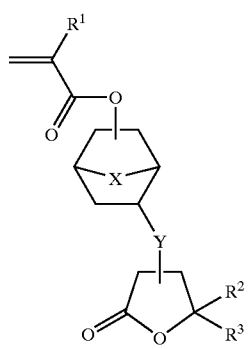

wherein $R^1$ is hydrogen or methyl, $R^2$ and $R^3$ each are hydrogen or a straight, branched or cyclic alkyl group having 1 to 15 carbon atoms, or $R^2$ and $R^3$, taken together, may form a ring and in that event, $R^2$ and $R^3$ together represent a straight, branched or cyclic alkylene group having 2 to 15 carbon atoms, X is —$CH_2$—, —$CH_2CH_2$— or —O— or two separate —H, and Y is —$(CH_2)_n$— in which at least one methylene group may be replaced by an oxygen atom, and n is an integer of 0 to 6.

3. A (meth)acrylate compound having the following general formula (3) or (4):

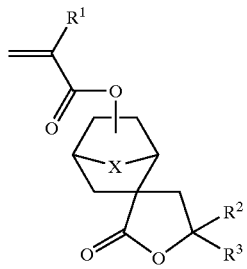

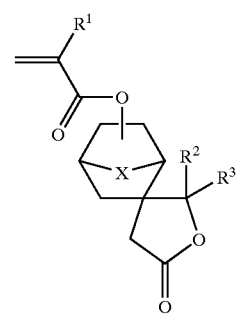

wherein $R^1$ is hydrogen or methyl, $R^2$ and $R^3$ each are hydrogen or a straight, branched or cyclic alkyl group having 1 to 15 carbon atoms, or $R^2$ and $R^3$, taken together, may form a ring and in that event, $R^2$ and $R^3$ together represent a straight, branched or cyclic alkylene group having 2 to 15 carbon atoms, and X is —$CH_2$—, —$CH_2CH_2$— or —O— or two separate —H.

4. A (meth)acrylate compound having the following general formula (5):

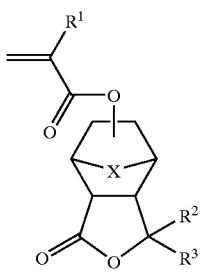

wherein $R^1$ is hydrogen or methyl, $R^2$ and $R^3$ each are hydrogen or a straight, branched or cyclic alkyl group having 1 to 15 carbon atoms, or $R^2$ and $R^3$, taken together, may form a ring and in that event, $R^2$ and $R^3$ together represent a straight, branched or cyclic alkylene group having 2 to 15 carbon atoms, and X is —$CH_2$—, —$CH_2CH_2$— or —O— or two separate —H, with the proviso that $R^2$ and $R^3$ are not simultaneously hydrogen if X is —$CH_2$.

5. A polymer comprising recurring units of the following general formula (6):

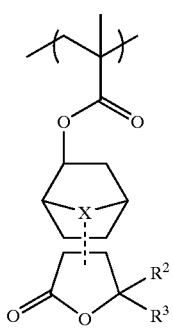

(6)

wherein R¹ is hydrogen or methyl, R² and R³ each are hydrogen or a straight, branched or cyclic alkyl group having 1 to 15 carbon atoms, or R² and R³, taken together, may form a ring and in that event, R² and R³ together represent a straight, branched or cyclic alkylene group having 2 to 15 carbon atoms, X is —CH₂—, —CH₂CH₂— or —O— or two separate —H, with the proviso that R² and R³ are not simultaneously hydrogen if X is —CH₂, and the broken line represents a single bond or divalent organic group that connects the norbornane ring, bicyclo[2.2.2] octane ring, 7-oxanorbornane ring or cyclohexane ring structure to the γ-butyrolactone ring structure, or a structure that shares one or two constituent carbon atoms between these ring structures.

6. The polymer of claim 5 further comprising recurring units of the following general formula (7):

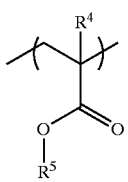

(7)

wherein R⁴ is hydrogen or methyl and R⁵ is a tertiary alkyl group having 4 to 20 carbon atoms, said polymer having a weight average molecular weight of 2,000 to 100,000.

7. A photoresist composition comprising (A) the polymer of claim 5,
(B) a photoacid generator, and
(C) an organic solvent.

8. A process for forming a resist pattern comprising the steps of:

applying the photoresist composition of claim 7 onto a substrate to form a film, heat treating the film and then exposing it to high-energy radiation having a wavelength of less than 300 nm or electron beams through a photo mask, and optionally heat treating the exposed film and developing it with a developer.

9. A polymer comprising recurring units of the formula:

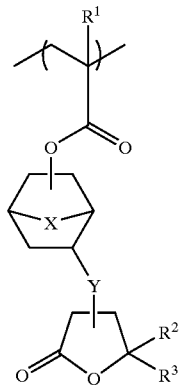

wherein R¹ is hydrogen or methyl, R² and R³ each are hydrogen or a straight, branched or cyclic alkyl group having 1 to 15 carbon atoms, or R² and R3, taken together, may form a ring and in that event, R² and R³ together represent a straight, branched or cyclic alkylene group having 2 to 15 carbon atoms, X is —CH₂—, —CH₂CH₂— or —O— or two separate —H, and Y is —(CH₂)ₙ— in which at least one methylene group may be replaced by an oxygen atom, and n is an integer of 0 to 6.

10. A polymer of claim 9 further comprising recurring units of the formula (7):

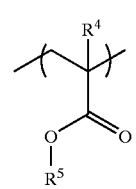

(7)

wherein R⁴ is hydrogen or methyl and R⁵ is a tertiary alkyl group having 4 to 20 carbon atoms, said polymer having a weight average molecular weight of 2,000 to 100,000.

11. A photoresist composition comprising (A) the polymer of claim 9,
(B) a photoacid generator, and
(C) an organic solvent.

12. A process for forming a resist pattern comprising the steps of:

applying the photoresist composition of claim 11 onto a substrate to form a film, heat treating the film and then exposing it to high-energy radiation having a wavelength of less than 300 nm or electron beams through a photo mask, and optionally heat treating the exposed film and developing it with a developer.

13. A polymer comprising recurring units of at least one of the formulae:

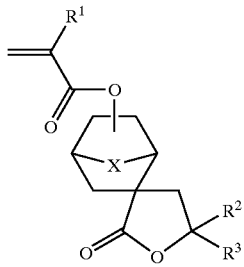
(3)

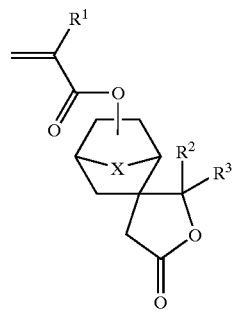
(4)

wherein $R^1$ is hydrogen or methyl, $R^2$ and $R^3$ each are hydrogen or a straight, branched or cyclic alkyl group having 1 to 15 carbon atoms, or $R^2$ and $R^3$, taken together, may form a ring and in that event, $R^2$ and $R^3$ together represent a straight, branched or cyclic alkylene group having 2 to 15 carbon atoms, and X is —$CH_2$—, —$CH_2CH_2$— or —O— or two separate —H.

14. The polymer of claim 13 further comprising recurring units of formula (7):

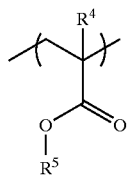
(7)

wherein $R^4$ is hydrogen or methyl and $R^5$ is a tertiary alkyl group having 4 to 20 carbon atoms, said polymer having a weight average molecular weight of 2,000 to 100,000.

15. A photoresist composition comprising:

A) the polymer of claim 13,
B) a photoacid generator, and
C) an organic solvent.

16. A process for forming a resist pattern comprising the steps of:
  applying the photoresist composition of claim 15 onto a substrate to form a film,
  heat treating the film and then exposing it to high-energy radiation having a wavelength of less than 300 nm or electron beams through a photo mask, and
  optionally heat treating the exposed film and developing it with a developer.

17. A photoresist composition comprising:
A) the polymer of claim 6,
B) a photoacid generator, and
C) an organic solvent.

18. A photoresist composition comprising:
A) the polymer of claim 10,
B) a photoacid generator, and
C) an organic solvent.

19. A photoresist composition comprising:
A) the polymer of claim 14,
B) a photoacid generator, and
C) an organic solvent.

20. A (meth)acrylate compound having the formula (1):

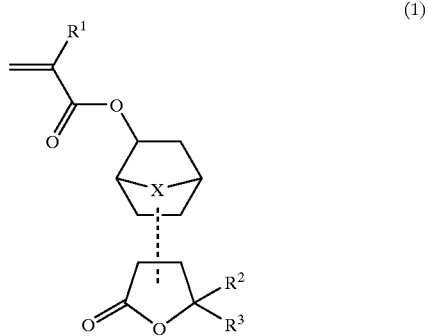
(1)

wherein (i) $R^1$ is hydrogen or methyl, (ii) $R^2$ and $R^3$ each are hydrogen or a straight, branched or cyclic alkyl group having 1 to 15 carbon atoms, or $R^2$ and $R^3$, taken together, form a ring where $R^2$ and $R^3$, together represent a straight, branched or cyclic alkylene group having 2 to 15 carbon atoms, and X is —$CH_2CH_2$— or —O— or two separate —H, (iii) $R^2$ is hydrogen or a straight, branched or cyclic alkyl group having 1 to 15 carbon atoms, $R^3$ is a straight, branched or cyclic alkyl group having 1 to 15 carbon atoms, or $R^2$ and $R^3$, taken together, form a ring where $R^2$ and $R^3$ together represent a straight, branched or cyclic alkylene group having 2 to 15 carbon atoms, and X is —$CH_2$—, and (iv) the broken line represents a single bond or divalent organic group that connects the norbornane ring, bicyclo [2.2.2] octane ring, 7-oxanorbornane ring or cyclohexane ring structure to the γ-butyrolactone ring structure, or a structure that shares one or two constituent carbon atoms between these ring structures.

\* \* \* \* \*